United States Patent
Dasbach et al.

(10) Patent No.: US 12,337,158 B2
(45) Date of Patent: Jun. 24, 2025

(54) APPARATUS FOR REMOVING AND RETAINING A NEEDLE SHIELD

(71) Applicant: SANOFI, Paris (FR)

(72) Inventors: Uwe Dasbach, Frankfurt am Main (DE); Thomas Mark Kemp, Melbourn Herts (GB); Louise Hodgson, Melbourn Herts (GB); Frederick Harrison, Melbourn Herts (GB); George Edward Sykes, Melbourn Herts (GB)

(73) Assignee: Sanofi, Paris (FR)

( * ) Notice: Subject to any disclaimer, the term of this patent is extended or adjusted under 35 U.S.C. 154(b) by 954 days.

(21) Appl. No.: 16/766,251

(22) PCT Filed: Nov. 15, 2018

(86) PCT No.: PCT/EP2018/081306
§ 371 (c)(1),
(2) Date: May 21, 2020

(87) PCT Pub. No.: WO2019/101613
PCT Pub. Date: May 31, 2019

(65) Prior Publication Data
US 2021/0154416 A1 May 27, 2021

(30) Foreign Application Priority Data
Nov. 23, 2017 (EP) ..................... 17306622

(51) Int. Cl.
*A61M 5/32* (2006.01)
*A61M 5/24* (2006.01)

(52) U.S. Cl.
CPC ............ *A61M 5/3204* (2013.01); *A61M 5/24* (2013.01); *A61M 5/3202* (2013.01)

(58) Field of Classification Search
CPC ..... A61M 5/3204; A61M 5/24; A61M 5/3202
See application file for complete search history.

(56) References Cited

U.S. PATENT DOCUMENTS

| 5,098,400 A | 3/1992 | Crouse et al. |
| 9,333,305 B2 * | 5/2016 | McLoughlin ....... A61M 5/3213 |

(Continued)

FOREIGN PATENT DOCUMENTS

| EP | 2886144 | 6/2015 |
| JP | 2016-540584 | 12/2016 |

(Continued)

OTHER PUBLICATIONS

PCT International Preliminary Report on Patentability in Application No. PCT/EP2018/081306, dated May 26, 2020, 7 pages.

(Continued)

*Primary Examiner* — Nathan R Price
*Assistant Examiner* — Tania Ismail
(74) *Attorney, Agent, or Firm* — Fish & Richardson P.C.

(57) ABSTRACT

An apparatus is arranged to receive and retain a needle shield for a medicament delivery device, the apparatus comprising a body comprising a wall defining a void and an opening in a proximal end of the body, the opening arranged to allow at least a part of the needle shield to be received into, and at least partially fill, the void, and arms extending from the wall into the void, wherein the arms are configured to engage the needle shield when the needle shield is received in the void and prevent the needle shield from being withdrawn from the void through the opening in the proximal end and wherein at least one of the arms has a first angle with respect to the wall and at least one of the arms has a second angle with respect to the wall that is different to the first angle.

17 Claims, 5 Drawing Sheets

(56) References Cited

U.S. PATENT DOCUMENTS

2009/0182284 A1   7/2009  Morgan
2014/0343503 A1  11/2014  Holmqvist
2016/0325051 A1  11/2016  Keim et al.

FOREIGN PATENT DOCUMENTS

| JP | 2017-504422 | 2/2017 |
| TW | 201726194 | 8/2017 |
| TW | 201729859 | 9/2017 |
| WO | WO 2015/091850 | 6/2015 |
| WO | WO 2015/113968 | 8/2015 |
| WO | WO 2016/193353 | 12/2016 |
| WO | WO 2017/089261 | 6/2017 |
| WO | WO 2017/089263 | 6/2017 |
| WO | WO 2017/089266 | 6/2017 |

OTHER PUBLICATIONS

PCT International Search Report and Written Opinion in Application No. PCT/EP2018/081306, dated Feb. 5, 2019, 11 pages.
Third Party Observations in European Appln. No. 18800197.8, mailed Aug. 25, 2022, 32 pages.

* cited by examiner

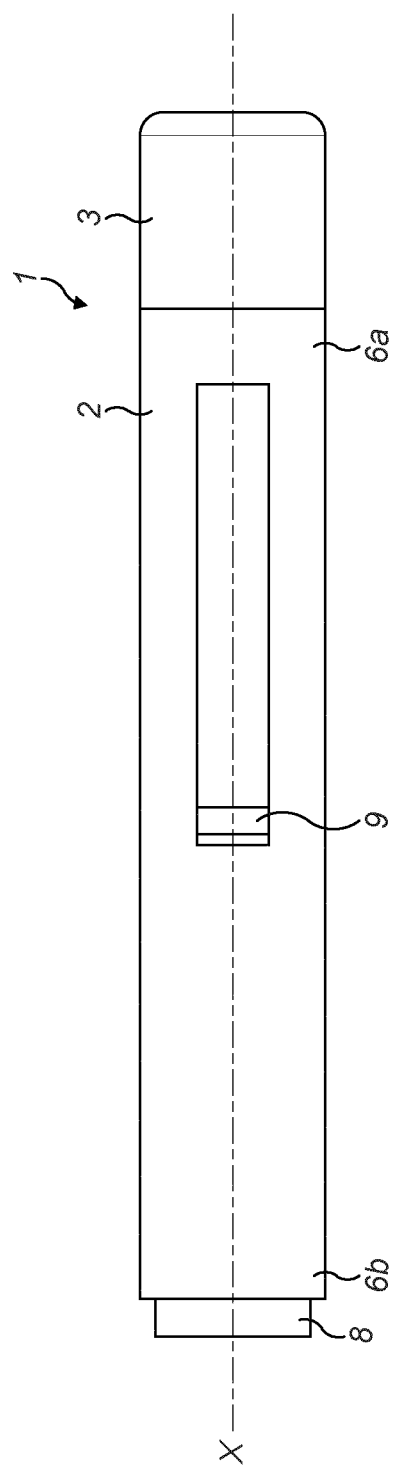
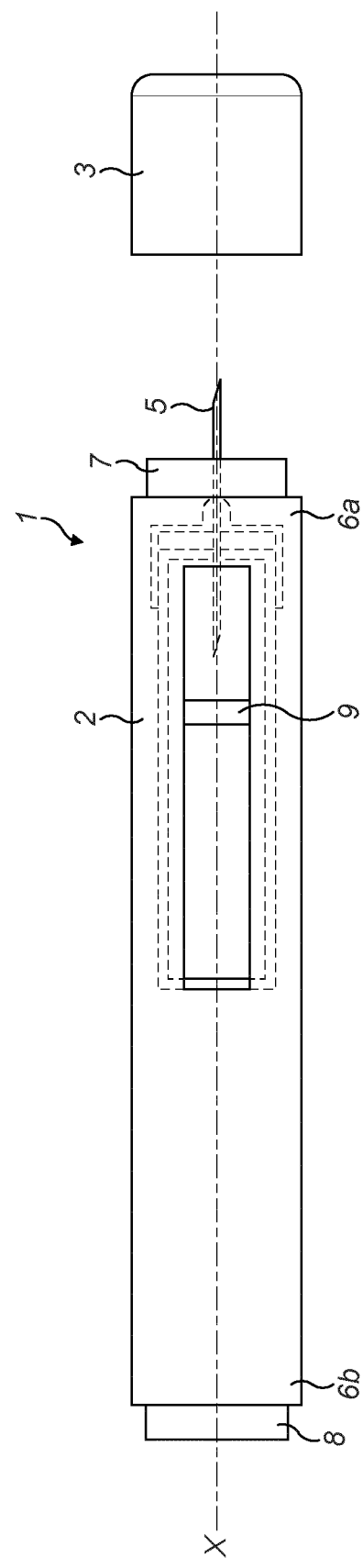

APPARATUS FOR REMOVING AND RETAINING A NEEDLE SHIELD

CROSS REFERENCE TO RELATED APPLICATIONS

The present application is the national stage entry of International Patent Application No. PCT/EP2018/081306, filed on Nov. 15, 2018, and claims priority to Application No. EP 17306622.6, filed on Nov. 23, 2017, the disclosures of which are incorporated herein by reference.

FIELD OF INVENTION

The present disclosure relates to apparatus for removing and retaining a needle shield of a medicament delivery device.

BACKGROUND

Medicament delivery devices, such as auto-injectors, are known in the art for dispensing a medicament to the injection site of a patient. Such injection devices typically comprise a body, a needle shield and a cap. A needle syringe is located in the body. The needle shield covers the needle, whilst the cap is removably attached to the body and covers the needle shield. To dispense the medicament, the cap and shield are first removed from the body to expose the needle. The needle is then inserted into the body of the patient at the injection site to dispense the medicament.

The needle shield covers and protects the needle from contamination. This ensures that the needle is kept sterile and also prevents the sharp needle from causing injury. However, in order to use the medicament delivery device, it is first necessary to remove the needle shield from the needle. This carries the risk that patient may unintentionally succumb to needle stick injuries. Furthermore, owning to the relatively small dimensions of the needle shield, the needle shield can be difficult to remove from the body prior to injection, particularly if the patient is elderly or infirm.

SUMMARY

According to a first aspect, there is provided an apparatus arranged to receive and retain a needle shield for a medicament delivery device, the apparatus comprising: a body comprising a proximal end, a distal end and a wall extending between the proximal end and the distal end, wherein the wall defines a void and proximal edges of the wall define an opening in the proximal end of the body, the opening arranged to allow at least a part of the needle shield to be received into, and at least partially fill, the void; and two or more resiliently deformable arms extending from the wall into the void, wherein the arms are configured to engage the needle shield when the needle shield is received in the void and prevent the needle shield from being withdrawn from the void through the opening in the proximal end and wherein at least one of the arms has a first angle with respect to the wall and at least one of the arms has a second angle with respect to the wall that is different to the first angle.

In some embodiments, at least one of the arms is of a first length and at least one of the arms is of a second length that is different to the first length.

In some embodiments, the angle formed between the arms of the first length and the wall defines the first angle and the angle formed between the arms of the second length and the wall defines the second angle.

In some embodiments, at least one of the arms defines a first angle with respect to the wall and at least one of the arms defines a second angle with respect to the wall that is different to the first angle when each of the two or more arms is in engagement with the needle shield.

In some embodiments, at least one of the arms of the first length is adjacent to at least one of the arms of the second length.

In some embodiments, the arms are arranged to deform when at least a part of the needle shield is received by the arms.

In some embodiments, the arms are arranged to form an interference fit with the needle shield when at least a part of the needle shield is received by the arms.

In some embodiments, each of the arms comprises an engaging region arranged to engage with an external surface of the needle shield.

In some embodiments, the shape of the engaging region complements the shape of the external surface of the needle shield.

In some embodiments, the engaging region is arc-shaped.

In some embodiments, the apparatus is arranged to be received into and be retained within a cap for a medicament delivery device.

In some embodiments, the wall comprises one or more openings arranged to engage with protrusions formed within the cap so as to prevent the apparatus from being removed from the cap.

In some embodiments, the wall is arranged to deform when the apparatus is received into the cap to allow the protrusions formed on the cap to engage with the openings in the wall.

In some embodiments, at least a part of the wall is formed from a resiliently deformable material.

In some embodiments, the apparatus is arranged to be aligned in a pre-defined position with respect to the cap.

In some embodiments, the body comprises an orientation element for aligning the apparatus in a predefined position with respect to the cap.

In some embodiments, the orientation element is disposed at the distal end of the body and arranged to engage with a projection located within the cap.

In some embodiments, the apparatus has a generally cylindrical or tubular shape.

According to a second aspect there is provided a blank arranged to be assembled into an apparatus for receiving and retaining a needle shield of a medicament delivery device, the blank comprising: a section of sheet material comprising a proximal edge in generally parallel alignment with a distal edge, the distal edge comprising one or more ridges; one or more openings located in the sheet; and two or more arms comprised within the sheet and at least partially obscuring the one or more openings.

In some embodiments, the blank is arranged to be assembled into the apparatus of the first aspect.

According to a third aspect there is provided a medicament delivery device comprising the apparatus according to the first aspect and a medicament containing cartridge.

In some embodiments, the medicament delivery device is an auto-injector.

According to a fourth aspect there is provided a method of manufacturing the apparatus according to the first aspect as using the blank according to the second aspect.

According to a fifth aspect there is provided a cap for a medicament delivery device, wherein the cap is arranged to receive and retain the apparatus according to the first aspect.

According to a sixth aspect there is provided a system comprising the cap according to the fifth aspect and the apparatus according to the first aspect.

BRIEF DESCRIPTION OF FIGURES

FIGS. 1a and 1b show an injection device for use with the apparatus for removing a needle shield;

DETAILED DESCRIPTION

Figure 2:
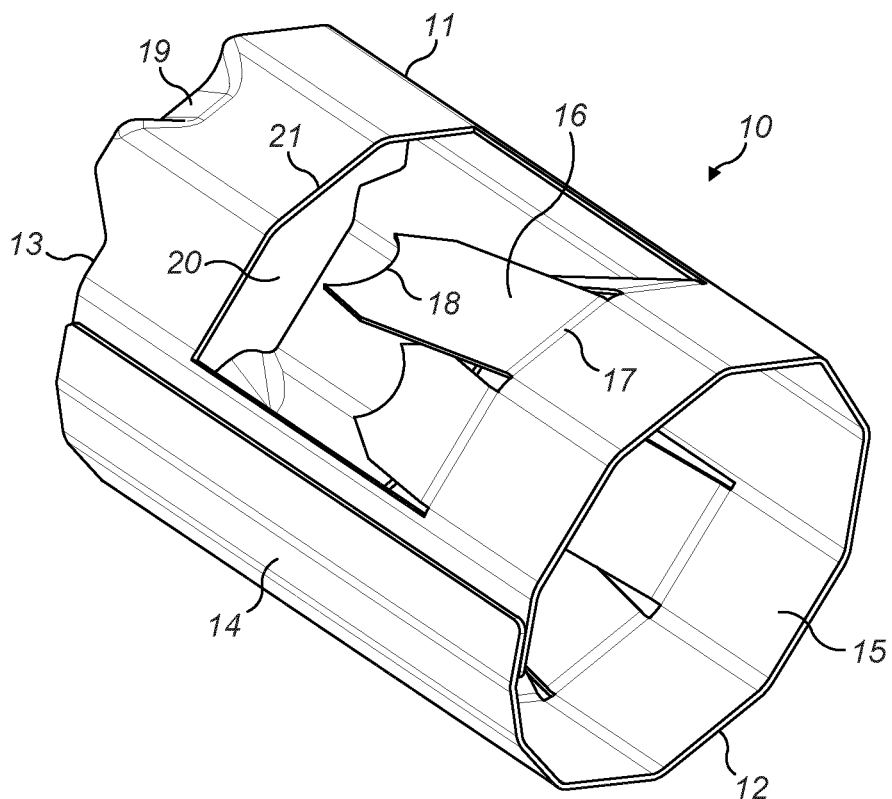
FIG. 2 depicts the apparatus for removing the needle shield.

Embodiments of the present invention provide apparatus for receiving and retaining a needle shield of a medicament delivery device, such as an injection device or an auto-injector device. The apparatus includes a body with two or more arms for engaging with a needle shield covering the needle of the medicament delivery device. The medicament delivery device comprises a cap and the apparatus can be disposed inside the cap.

The arms attach to the needle shield as the cap is pushed onto the medicament delivery device, and retain the needle shield within the cap when the cap is removed from the device. The apparatus provides an improved injection device which does not require the needle shield to be separately removed from the needle.

A medicament delivery device, as described herein, may be configured to inject a medicament into a patient. For example, delivery could be sub-cutaneous, intramuscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device. The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary medicament delivery device 1 is shown in FIGS. 1A & 1B. Device 1, as described above, is configured to inject a medicament into a patient's body. Device 1 includes a housing 2 which typically contains a reservoir containing the medicament to be injected (e.g., a syringe) and the components required to facilitate one or more steps of the delivery process. Device 1 can also include a cap assembly 3 that can be detachably mounted to the housing 2. Typically a user must remove cap 3 from housing 2 before device 1 can be operated.

A needle shield 4 (not shown) covers the needle 5 of the device 1. The outer surface of the needle shield may be made from a flexible, relatively soft or malleable material, such as rubber, or a hard, rigid material, such as plastic. In order to expose the needle 5, it is necessary to remove the needle shield 4.

As shown, housing 2 is substantially cylindrical and has a substantially constant diameter along the longitudinal axis X. The housing 2 has a distal region 6a and a proximal region 6b. The term "distal" refers to a location that is relatively closer to a site of injection, and the term "proximal" refers to a location that is relatively further away from the injection site.

Device 1 can also include a needle sleeve 7 coupled to housing 2 to permit movement of sleeve 7 relative to housing 2. For example, sleeve 7 can move in a longitudinal direction parallel to longitudinal axis X. Specifically, movement of sleeve 6 in a proximal direction can permit a needle 5 to extend from distal region 6a of housing 2.

Insertion of needle 5 can occur via several mechanisms. For example, needle 5 may be fixedly located relative to housing 2 and initially be located within an extended needle sleeve 7. Proximal movement of sleeve 7 by placing a distal end of sleeve 7 against a patient's body and moving housing 2 in a distal direction will uncover the distal end of needle 5. Such relative movement allows the distal end of needle 5 to extend into the patient's body. Such insertion is termed "manual" insertion as needle 5 is manually inserted via the patient's manual movement of housing 2 relative to sleeve 7.

Another form of insertion is "automated," whereby needle 5 moves relative to housing 2. Such insertion can be triggered by movement of sleeve 7 or by another form of activation, such as, for example, a button 8. As shown in FIGS. 1A & 1B, button 8 is located at a proximal end of housing 2. However, in other embodiments, button 8 could be located on a side of housing 2.

Other manual or automated features can include drug injection or needle retraction, or both. Injection is the process by which a bung or piston 9 is moved from a proximal location within a syringe (not shown) to a more distal location within the syringe in order to force a medicament from the syringe through needle 5. In some embodiments, a drive spring (not shown) is under compression before device 1 is activated. A proximal end of the drive spring can be fixed within proximal region 6b of housing 2, and a distal end of the drive spring can be configured to apply a compressive force to a proximal surface of piston 9. Following activation, at least part of the energy stored in the drive spring can be applied to the proximal surface of piston 9. This compressive force can act on piston 9 to move it in a distal direction. Such distal movement acts to compress the liquid medicament within the syringe, forcing it out of needle 5.

Following injection, needle 5 can be retracted within sleeve 7 or housing 2. Retraction can occur when sleeve 7 moves distally as a user removes device 1 from a patient's body. This can occur as needle 5 remains fixedly located relative to housing 2. Once a distal end of sleeve 7 has moved past a distal end of needle 5, and needle 5 is covered, sleeve 7 can be locked. Such locking can include locking any proximal movement of sleeve 7 relative to housing 2.

Another form of needle retraction can occur if needle 5 is moved relative to housing 2. Such movement can occur if the syringe within housing 2 is moved in a proximal direction relative to housing 2. This proximal movement can be achieved by using a retraction spring (not shown), located in distal region 6a. A compressed retraction spring, when activated, can supply sufficient force to the syringe to move it in a proximal direction. Following sufficient retraction, any relative movement between needle 5 and housing 2 can be locked with a locking mechanism. In addition, button 8 or other components of device 1 can be locked as required.

With reference to FIG. 2, apparatus 10 arranged to receive and retain a needle shield (not shown) of a medicament delivery device is shown. The apparatus comprises a body 3 having a proximal end 12 and a distal end 13. The body may have a generally cylindrical or tubular shape. Alternatively, the body may have a variety of other shapes, such as cubic or cuboid.

Extending between the proximal end 12 and the distal end 13 is a wall 14. The proximal edge of the wall 14 defines an opening 15 in the proximal end 12 of the body 11. The wall 14 also defines a void or cavity in the body 12. The opening 15 has dimensions which permit the entry of a needle shield into the void that is defined by the wall 14. When the needle shield is received in the void via opening 15, it at least partially fills the void.

The apparatus 10 further comprises two or more arms 16 that extend radially inwards from the wall into the void towards a central axis of the body 11. The arms 16 extend in a distal direction towards the distal end of the body 11. The arms 16 project inwardly into void so that they contact the outer surface of a needle shield (not shown) when it is received in the void. Each of the arms 16 has a first end 17 which is connected to the wall 14 and a second end 18 which is arranged to engage with the needle shield when the needle shield is at least partially inserted into the void defined by the wall 14. Each arm 16 is positioned directly next to another arm, i.e. the arms are disposed side-by-side in the same cross-sectional plane of the wall 14. In alternative embodiments, each arm 16 may extend into the void from a variety of different locations between the proximal end 12 and distal end 13 of the body 11.

The distal edge of the wall 14 defines a second opening opposite the opening in the proximal end of the body 11. The distal edge also comprises an orientation element 19 in the form of a ridge or tab which is arranged to facilitate the insertion of the apparatus 10 into the cap. In alternative embodiments, the orientation element 19 may comprise more than one ridge.

The apparatus 10 comprises one or more windows 20 which are located in the wall 14 of the body 11. The window(s) 20 comprises an edge 21 located towards the distal end 13 of the body 12.

Figure 3:
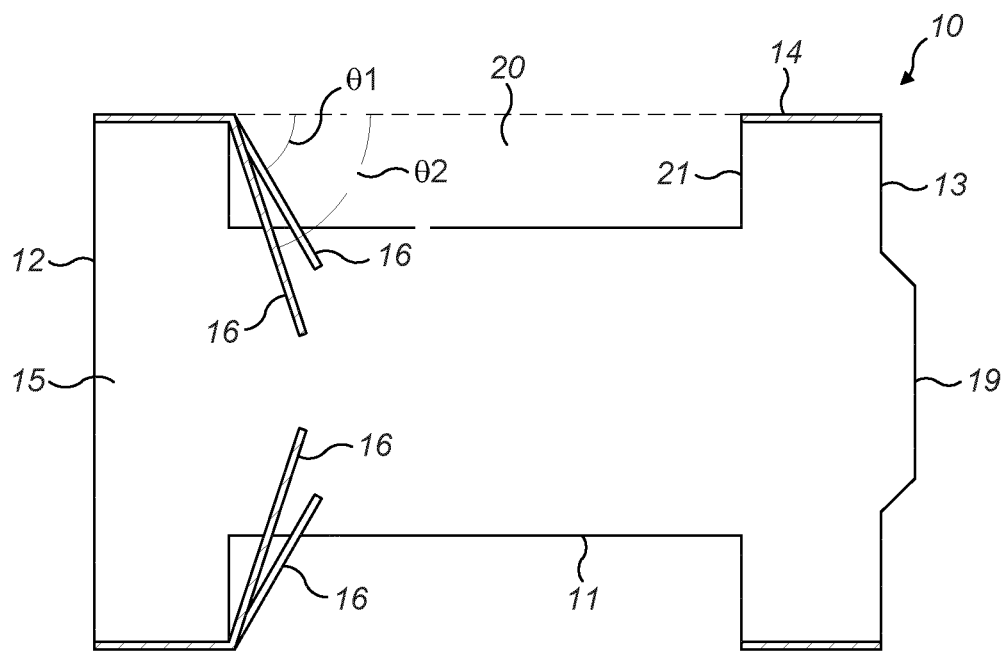
FIG. 3 shows a cross-sectional view of the apparatus for removing the needle shield.

FIG. 3 shows the apparatus in cross-section. Where the arms 16 are disposed on the same cross-sectional plane of the wall 14 (i.e. side-by-side), the second ends of the arms 16 may clash. The angle formed between the wall 14 and the arms 16 is known as the bend angle. In order to prevent clashing of the arms, the arms 16 may have a variety of different bend angles. That is to say, the angle formed between each of the arms 16 and the wall 14 can vary between different arms 16. In some embodiments, at least one of the arms 16 has a first bend angle $\theta 1$ with respect to the wall 14 and at least one of the arms 16 has a second bend angle $\theta 2$ with respect to the wall 14 that is different to the first angle. Where the arms are disposed side-by-side in the same cross-sectional plane of the wall 14, the apparatus is easier to manufacture because less complex tooling is required.

Using arms having different bend angles also allows the apparatus 10 to be used with a variety of different needle shields having different outer diameters. By increasing the bend angle between the wall 14 and the arms 16, the arms 16 will project further into the void. This means that the arms 16 can be arranged to grip needle shields which have a relatively narrow outer diameter. Conversely, decreasing the angle between the wall 14 and the arms 16 decreases the distance by which the arms 16 project into the void. This therefore enables the arms 16 to be arranged to grip needle shields which have a relatively wide diameter. A number of the arms 16 may have a first bend angle $\theta 1$ that is less than the second bend angle $\theta 2$ of a number of other arms. Where the bend angle varies between the arms, the apparatus can be used to remove needle shields having a variety of outer diameters. This is advantageous because only one apparatus is required to remove different diameter needle shields, i.e. the apparatus may be described as "universal".

The bend angles of the arms may be between 1 degree and 90 degrees, or about 1, 2, 3, 4, 5, 6, 7, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90 degree(s).

In some embodiments, the first bend angle is greater than the second bend angle. For example, the first bend angle can be between about 30 to about 60 degrees and the second bend angle can be between about 10 and about 29 degrees. In an embodiment, the first bend angle is about 25, 25.5, 26, 26.5, 27, 27.5, 28, 28.5, 29 or 29.5 degrees and the second bend angle is about 35, 35.5, 36, 36.5, 37, 37.5, 38, 38.5, 39, 39.5, 40, 40.5, 41, 41.5, 42, 42.5, 43, 43.5, 44, 44.5 or 45 degrees. A first bend angle of about 27.5 degrees and a second bend angle of about 42.5 degrees has been found particularly effective at gripping and retaining the needle shield.

Each of the arms 16 may have the same length or the arms 16 may be of different lengths. For example, one or more of the arms 16 may have a first length and one or more of the arms 16 may have a second length that is different to the first length.

Where the arms 16 have a variety of different lengths, the apparatus may be suitable for removing needle shield that have a variety of different outer diameters. This removes the needle to have multiple different needle shield removal devices, thereby simplifying the manufacturing process and reducing costs. The length of an arm may be defined as the measurement between the first end 17 of the arm and the second end 18 of the arm.

In some embodiments, the first length is greater than the second length. In some embodiments, the first length is between about 5 mm and 7 mm and the second length is between about 3 mm and 5 mm. A first length of about 5.75 mm and a second length of about 3.75 mm has been found to be particularly effective at gripping and retaining the needle shield.

When the needle shield is inserted into the void or cavity of the body 12, it engages the arms 16. The arms 16 may be pushed back when the needle shield is inserted into the void or cavity so as to decrease their bend angles with respect to the wall 14. When the needle shield is inserted into the void such that its outer surface engages the arms, at least one of the arms has a first bend angle and at least one of the arms has a second bend angle that is different to the first bend angle.

Referring again to FIG. 2, the second end 18 of the arms 16 has a needle shield engaging region. The needle shield engaging region of the arms 16 may be arranged to conform to the shape of the needle shield. For example, where the needle shield is generally cylindrical and thus has a generally circular cross section, the second end of the arms 16 may be generally arc shaped. This increases the contact area between the arms 16 and the outer surface of the needle shield, which thereby increases the friction between the arms 16 and the needle shield and further reduces the possibility of withdrawing the needle shield from the apparatus 10 through the opening 15 in the proximal end of the body 11. The arrangement of the arms 16 removes the need for a region of material between adjacent arms, i.e. there are no "ribs" between adjacent arms 26. This simplifies manufacturing of the apparatus.

Figure 4:
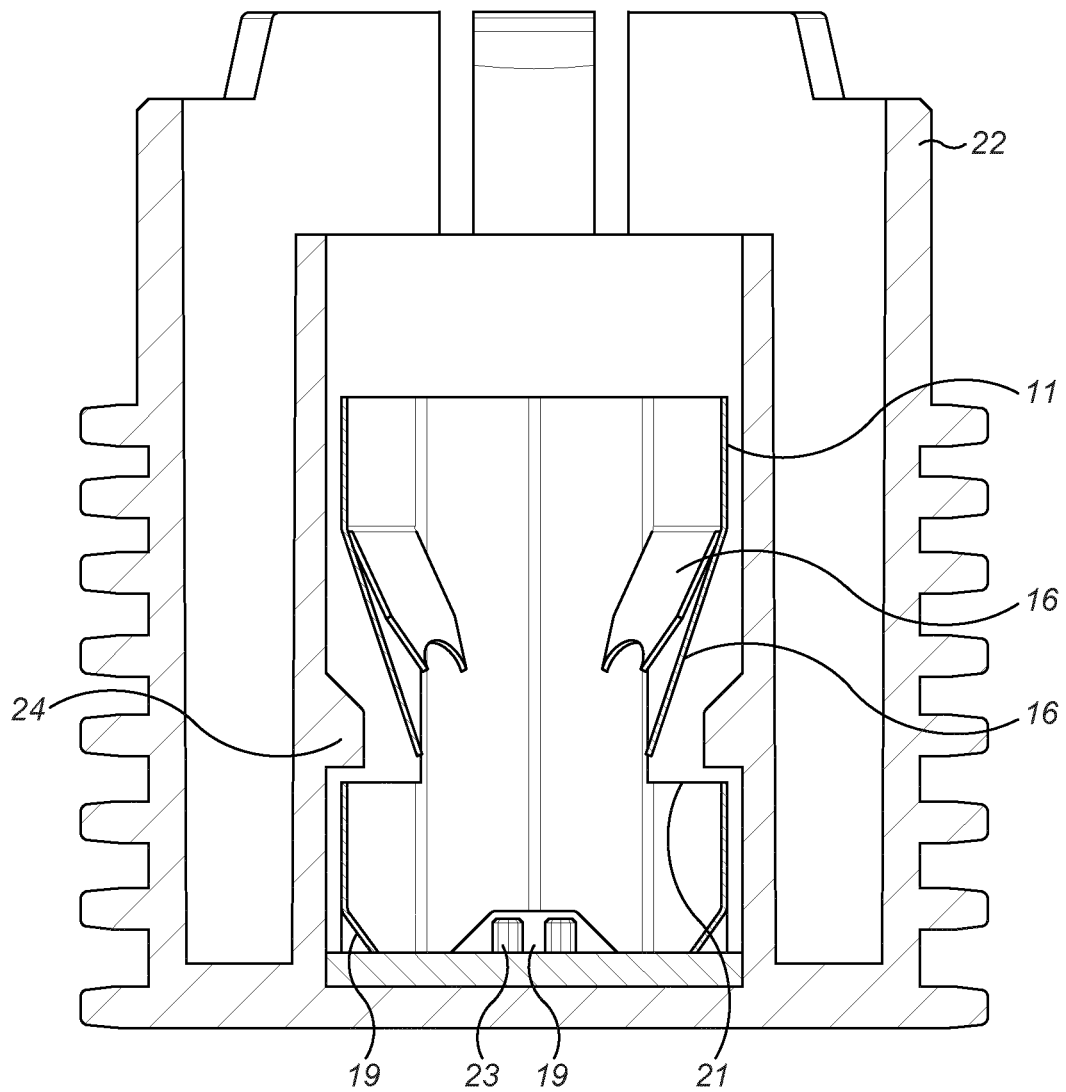
FIG. 4 shows a cross-sectional view of a cap containing the apparatus for removing the needle shield.

As shown in FIG. 4, the body 11 of the apparatus 10 is arranged to be received into and retained in a cap 22 for a medicament delivery device. It is important to ensure that the apparatus 10 is received into the cap 22 in a particular orientation. The orientation element 19 facilitates insertion of that the apparatus into the cap in a predefined position with respect to the cap 22. The orientation element is angled with respect to the wall of the body 10 and aids insertion of the body 11 of the apparatus 10 into the cap 22 during assembly. The cap may comprise a cap alignment feature 23, such as a slot or crevice, which is located inside the cap 22, and which further aids alignment of the apparatus 10.

When the apparatus is received into the cap 22 for the medicament delivery device, it is important to ensure that the apparatus cannot be readily removed from the cap 22. In order to prevent the apparatus 10 from being removed from the cap 22, the edge 21 of the window(s) 20 is arranged to engage with one or more projections 24 formed within the cap 22. When the apparatus 10 is received into the cap 22 in a distal direction, the projections 24 extend through the window(s) 20 and into the void defined by the wall 14. The edge 21 of the window(s) 20 can abut the flat portion of the projection(s) 24 thereby preventing the apparatus 10 from being removed from the cap 22. The window(s) 21 rotationally locks the apparatus 10 with respect to the cap 22 and therefore prevents axial rotation of the apparatus when it is received in the cap 22.

In order to allow the projection(s) 24 to be received through the window(s) 20 of the body into the void of the apparatus, the distal end 13 of the body 11 slides over the projection(s) 24 during insertion of the apparatus 10 into the cap 22 of the medicament delivery device until the projection(s) 24 is received into the window(s) 20. As the apparatus 10 is inserted into the cap 22, owing to the angled nature of the orientation element 19, the orientation element 19 begin to slide over the surface of the protrusion(s) 24. In other words, the orientation element 19 act as a "lead-in" component and thus facilitates movement of the apparatus 10 into the cap 22. As the apparatus 10 continues to be inserted into the cap 22, the sliding action of the body 10 over the protrusion(s) 24 causes the body 11 of the apparatus 10 to deform slightly until the protrusion(s) 24 are received into the windows 20 of the apparatus 10. At this point, the body may substantially revert back to its initial shape. As the orientation element 19 is disposed along the distal edge of the body only, the apparatus 10 may only be inserted into the cap 19 in one orientation (i.e. it cannot be inserted "upside down").

As mentioned, at least part of the body 11 to deform when it is being inserted into the cap 22 in order to allow for the projection(s) 24 to be received into the window(s) 20. This may be achieved by forming at least part of the body 11 from a material that can deform to allow the projection(s) 24 to be received into the window(s) 20, and then revert back to its previous shape. For example, the body 11 may be formed from a relatively thin sheet of metal or plastic that is resiliently deformable. In order for the arms 16 to deform when the needle shield 4 is received into the apparatus 10, the arms 16 are bent by the force of needle shield 4. The arms 16 may be formed of a resiliently deformable material.

The shape of the body 11 may vary depending upon the shape of the needle shield to be removed from the medicament delivery device, or the shape of the cap. For example, where the needle shield has a generally cylindrical shape, the body 11 may also have a generally cylindrical shape. The shape of the body 11 may alternatively be generally cubic or cuboid such that the apparatus 10 can fit into a generally cubic or cuboid recess in the cap.

Figure 5:
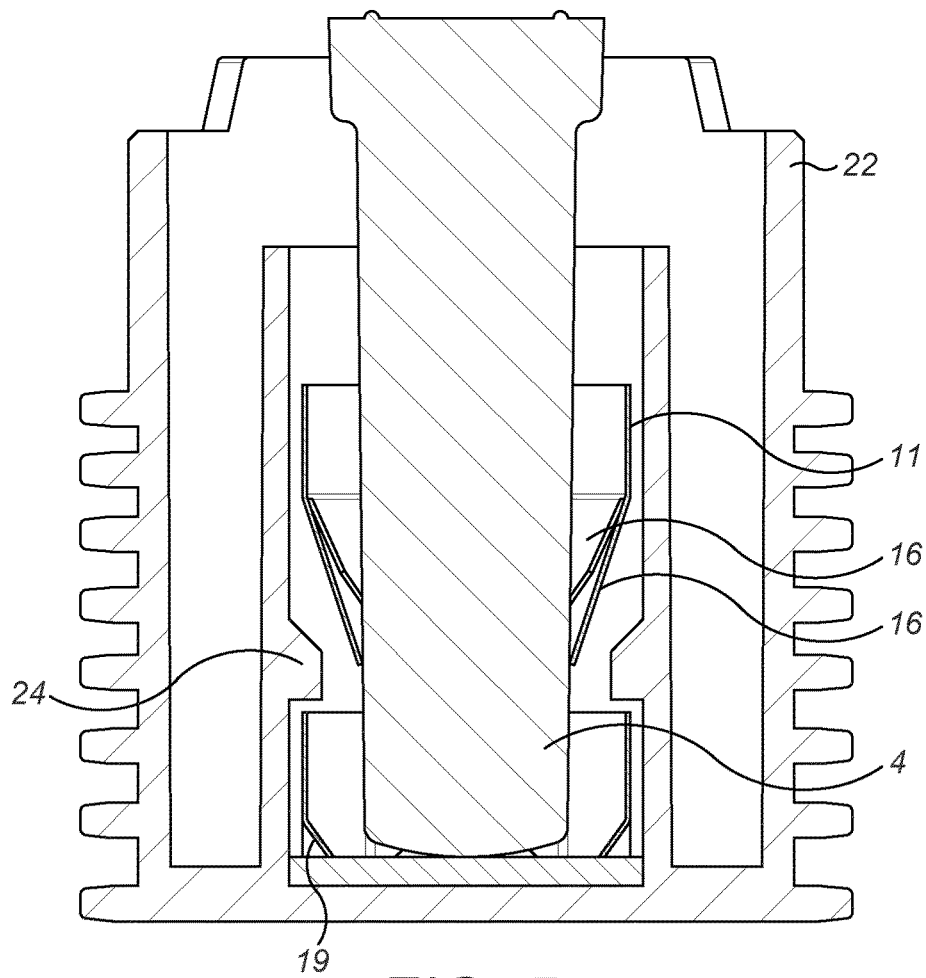
FIG. 5 shows a cross-sectional view of the cap containing the apparatus for removing the needle shield when the needle shield is inserted into the apparatus.

As shown in FIG. 5, the needle shield 4 of the medicament delivery device is received into the apparatus 10. The arms 16 of the apparatus 10 engage with outer surface of the needle shield 4. The arms 16 of the apparatus 10 form an interference fit with the needle shield 4. When the cap 22 is pushed onto the distal end of the injection device, the needle shield 4 is received through the opening at the proximal end of the apparatus 10 and into the void. As the needle shield 4 is inserted into the apparatus 10 the arms 16 engage with the outer surface of the needle shield 4. When the needle shield 4 is fully received into the void, the cap 3 seals the injection device 1 and protects the needle 5 before the injection device 1 is used.

The arms 16 of the apparatus are angled towards the distal end of the apparatus 10 and are compressed by the needle shield 4 thereby allowing the needle shield 4 to be received into the apparatus 10 in a distal direction. The arms 16 remain in contact with the needle shield 4 while the apparatus 10 remains on the injection device.

The cap 3, and thus the apparatus 10, is removed from the injection device before it can be used. The arms 16 of the apparatus 10 are in contact with the needle shield 4 and are angled towards the distal end of the injection device 1. When the apparatus 10 is moved distally, the engaging region of each arm 16 engages with the outer surface of the needle shield 4. The needle shield 4 is retained by the arms 16, which exert a force to push the needle shield 4 in the distal direction, thereby preventing the needle shield 4 from being removed through the opening in the proximal end 12 of the body.

As the apparatus 10 is removed from the injection device, the needle shield 4 is retained within the apparatus 10 by the arms 16 and is removed from the needle 5. The needle 5 of the medicament delivery device is therefore exposed when the needle shield 4 is removed and the injection device is ready for use.

As mentioned previously, needle shields can have either a relatively hard or a relatively soft outer surface. For example, some needle shields are made from a relatively hard plastic material, whilst others are made from a relatively soft and malleable material. Advantageously, owing to relative position of each arm 16 of the apparatus 10, the apparatus 10 is configured to receive and retain needle shields that are made from both hard and soft materials.

The apparatus 10 improves the usability of the injection device by providing means for the needle shield 4 to be removed at the same time as removing the cap 22. Furthermore, the external appearance of the cap 22 is the same as that of a conventional cap and does not require an additional opening at the distal end to remove the needle shield. As such, in appearance and in use the cap 22 appears normal to the user and therefore provides the improved operation of the injection device without additional complexity for the user.

Figure 6:
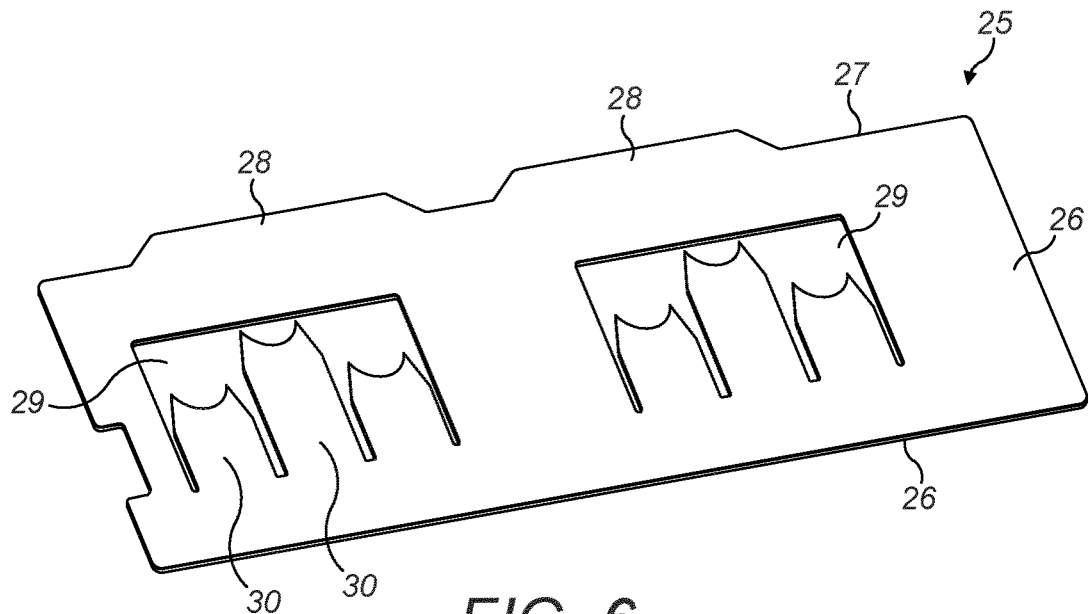
FIG. 6 shows a blank for assembly into the apparatus for removing the needle shield.

As shown in FIG. 6, the apparatus 10 is formed from a blank 25. The blank 25 can be formed from a substantially flat sheet of material or section of sheet material 26, such as a sheet of metal or hard plastic. The blank 25 can be formed by any suitable machining process, for example, by a pressing or cutting the blank from a larger sheet of material. The blank 25 has a proximal edge 26 in generally parallel alignment with a distal edge 27. The distal edge 27 of the blank 25 can comprise one more ridges 28 which will correspond to the orientation element 19 of the apparatus 10 when the blank is assembled into the apparatus 10. The blank 25 comprises one or more openings 29 and two or more arms 30. The opening(s) 29 will correspond to the window(s) 20 of the apparatus 10, and the arms 30 will correspond to the arms 16 of the apparatus 10. The arms 30 at least partially obscure the one or more openings 29.

The blank 25 can be assembled into the apparatus 10 by, for example, rolling or folding the blank to form the general shape of the apparatus 10. The arms 30 are then bent into position such they extend radially inwardly into the void formed by the walls 14 of the apparatus, thereby forming the arms 16 of the apparatus. Assembly of the blank 25 into the apparatus 10 is relatively straightforward because no other parts are required.

Forming the apparatus 10 from a blank 25 makes the manufacturing process relatively straightforward because the tooling required to form the blank is relatively simple. For example only a single press may be required to form the blank. It also means that only a single component (a single sheet of material) is required to form the apparatus 10, thereby reducing the cost of manufacturing the apparatus. As the apparatus 10 is easier to manufacture, relatively high manufacturing yields can be achieved.

Although a few embodiments of the present invention have been shown and described, it will be appreciated by those skilled in the art that changes may be made in these embodiments without departing from the invention, the scope of which is defined in the appended claims. Various components of different embodiments may be combined where the principles underlying the embodiments are compatible.

For example, the arms 16 may also be formed as a plurality of hooks which are directed inwards from the apparatus 10. A plurality of arms 16 of different forms may be used to ensure the needle shield is gripped tightly.

The apparatus 10 may be used as part of a cap for an auto-injector device which includes any of an automatic needle insertion mechanism, an automatic medicament dispensing mechanism or an automatic cap removal mechanism. Alternatively, the apparatus 10 may be part of a cap for a manual injection device in which a needle syringe is mounted to assist the user with a medicament delivery. Alternatively, the apparatus 10 may be used as a needle shield removal device (i.e. without the cap) to easily remove the needle shield from a syringe.

Figure 7B:
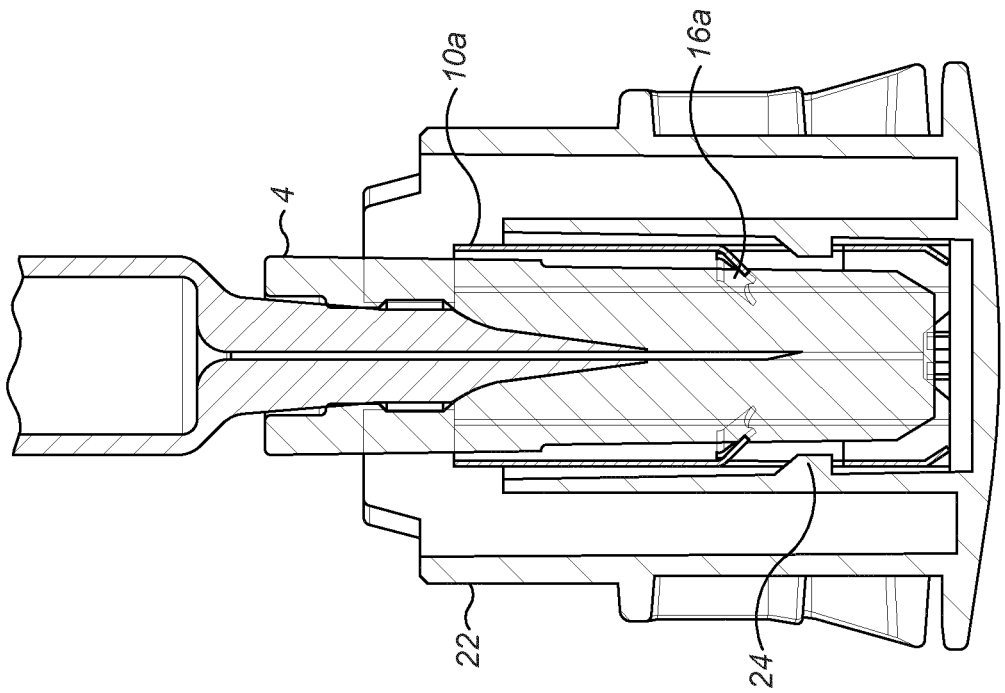
FIG. 7b shows a cross-sectional view of the cap containing a conventional needle shield removal apparatus.
Figure 7A:
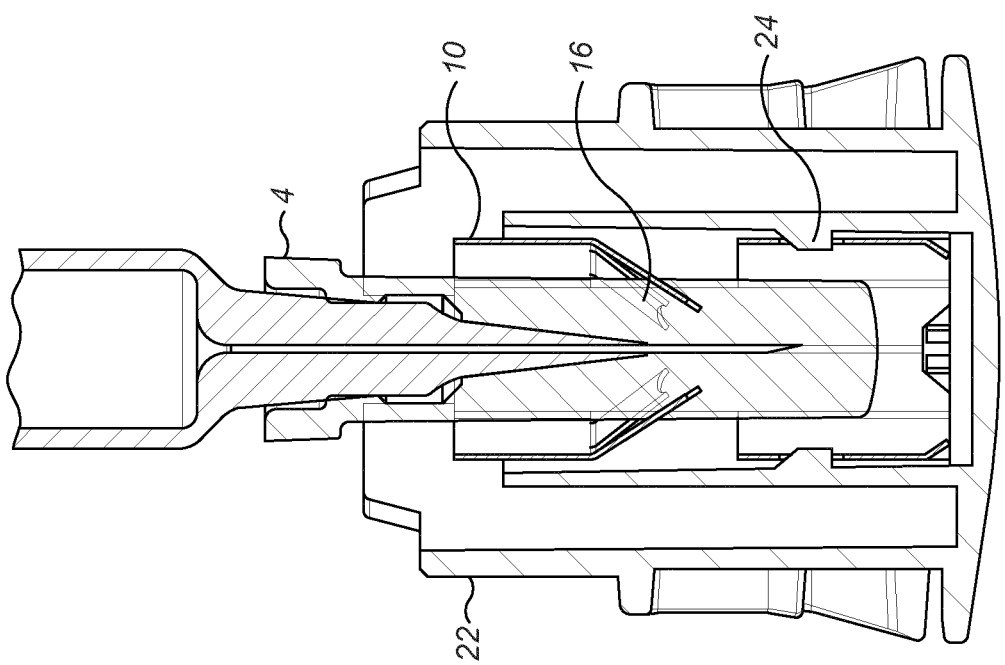
FIG. 7a shows a cross-sectional view of the cap containing the apparatus.

FIG. 7a shows the cap 22 with the apparatus 10 fitted to it. As mentioned previously, the cap 22 is a single component (i.e. it is one-piece) that comprises projections 24 which are configured to be received in windows 20 of the apparatus 10. Although the internal features of the cap 22 depicted in FIGS. 7a and 7b are identical to the internal features of the cap 22 depicted in FIGS. 4 and 5, the outer surface of the cap 22 depicted in FIGS. 7a and 7b is different to the outer surface of the cap 22 depicted in FIGS. 4 and 5. These differences are merely aesthetic and have no bearing on the operation of the cap 22 and its cooperation with the needle shield removal apparatus 10.

The cap 22 is also configured to receive a variety of different types of needle shield removal apparatus 10. For example, FIG. 7b shows the cap fitted with conventional needle shield removal apparatus 10a. As can be seen, the arms 16a are of the same length and the same angle. The specific position of the projections 24 means that the cap is compatible with existing needle shield removal apparatuses, as well as the apparatus 10 described herein (i.e. it may be described as a "universal cap"). Advantageously, this means that a single type of cap can be used for a variety of different needle shield removal apparatuses, thereby simplifying manufacturing of the cap 22 and reducing the overall manufacturing cost.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. An apparatus arranged to receive and retain a needle shield for a medicament delivery device, the apparatus comprising:
a body comprising a proximal end, a distal end, and a wall extending longitudinally between the proximal end and the distal end of the body, wherein the wall defines a void, and proximal edges of the wall define an opening in the proximal end of the body, the opening being arranged to allow at least a part of the needle shield to be received in, and at least partially fill, the void; and
two or more resiliently deformable arms adjacent each other, each of the two or more resiliently deformable arms extending from a first end connected to the wall towards the distal end of the body from a same transverse cross-sectional plane of the wall inwardly into the void, wherein each of the two or more resiliently deformable arms terminates in a second end, the second end of each of the two or more resiliently deformable arms being configured to engage the needle shield when the needle shield is received in the void and prevent the needle shield from being withdrawn from the void through the opening in the proximal end and wherein at least one of the two or more resiliently deformable arms has a first angle with respect to the wall and at least one of the two or more resiliently deformable arms has a second angle with respect to the wall that is different from the first angle when the needle shield is received in the void.

2. The apparatus of claim 1, wherein at least one of the two or more resiliently deformable arms is of a first length and at least one of the two or more resiliently deformable arms is of a second length that is different from the first length.

3. The apparatus of claim 2, wherein an angle formed between the at least one of the two or more resiliently deformable arms of the first length and the wall defines the first angle, and an angle formed between the at least one of the two or more resiliently deformable arms of the second length and the wall defines the second angle.

4. The apparatus of claim 2, wherein at least one of the two or more resiliently deformable arms of the first length is adjacent to at least one of the two or more resiliently deformable arms of the second length.

5. The apparatus of claim 1, wherein the two or more resiliently deformable arms are arranged to deform when at least a part of the needle shield is received by the two or more resiliently deformable arms.

6. The apparatus of claim 1, wherein each of the two or more resiliently deformable arms comprises an engaging region arranged to engage with an external surface of the needle shield.

7. The apparatus of claim 1, wherein the apparatus is arranged to be received into and be retained within a cap for a medicament delivery device.

8. The apparatus of claim 7, wherein the wall comprises one or more openings arranged to engage with protrusions formed within the cap so as to prevent the apparatus from being removed from the cap.

9. The apparatus of claim 8, wherein the wall is arranged to deform when the apparatus is received in the cap to allow the protrusions formed on the cap to engage with the one or more openings in the wall.

10. The apparatus of claim 8, wherein the one or more openings are arranged to engage with the protrusions formed within the cap so as to prevent axial rotation of the apparatus relative to the cap.

11. The apparatus of claim 7, wherein the apparatus is arranged to be aligned in a pre-defined position with respect to the cap.

12. The apparatus of claim 7, wherein the body comprises an orientation element for aligning the apparatus in a pre-defined position with respect to the cap.

13. The apparatus of claim 12, wherein the orientation element is disposed at the distal end of the body and arranged to engage with a projection located within the cap.

14. The apparatus of claim 1, wherein at least a part of the wall is formed from a resiliently deformable material.

15. The apparatus of claim 1, wherein the apparatus has a generally cylindrical or tubular shape.

16. A medicament delivery device comprising:
a medicament-containing cartridge;
a needle shield; and
an apparatus comprising
  a body comprising a proximal end, a distal end, and a wall extending between the proximal end and the distal end of the body, wherein the wall defines a void, and proximal edges of the wall define an opening in the proximal end of the body, the opening being arranged to allow at least a part of the needle shield to be received in, and at least partially fill, the void, and
  two or more resiliently deformable arms adjacent each other, each of the two or more resiliently deformable arms extending from a first end connected to the wall towards the distal end of the body from a same transverse cross-sectional plane of the wall inwardly into the void, wherein each of the two or more resiliently deformable arms terminates in a second end, the second end of each of the two or more resiliently deformable arms being configured to engage the needle shield when the needle shield is received in the void and prevent the needle shield from being withdrawn from the void through the opening in the proximal end and wherein at least one of the two or more resiliently deformable arms has a first angle with respect to the wall and at least one of the two or more resiliently deformable arms has a second angle with respect to the wall that is different from the first angle when the needle shield is received in the void.

17. The apparatus of claim 1, wherein the second end is a free end.

* * * * *